(12) United States Patent
Guo et al.

(10) Patent No.: US 11,860,135 B2
(45) Date of Patent: Jan. 2, 2024

(54) THREE-DIMENSIONAL DYNAMIC AND STATIC LOAD TEST SYSTEM FOR SIMULATING DEEP ROADWAY EXCAVATION AND METHOD THEREOF

(71) Applicant: Shandong University of Science and Technology, Qingdao (CN)

(72) Inventors: Weiyao Guo, Qingdao (CN); Yueying Zhang, Qingdao (CN); Lexin Chen, Qingdao (CN); Dongxiao Zhang, Qingdao (CN); Yunliang Tan, Qingdao (CN); Tongbin Zhao, Qingdao (CN)

(73) Assignee: SHANDONG UNIVERSITY OF SCIENCE AND TECHNOLOGY, Qingdao (CN)

( * ) Notice: Subject to any disclaimer, the term of this patent is extended or adjusted under 35 U.S.C. 154(b) by 0 days.

(21) Appl. No.: 18/317,198

(22) Filed: May 15, 2023

(65) Prior Publication Data

US 2023/0280251 A1 Sep. 7, 2023

Related U.S. Application Data

(63) Continuation of application No. PCT/CN2022/073324, filed on Jan. 22, 2022.

(51) Int. Cl.
*G01N 3/34* (2006.01)
*G01N 3/12* (2006.01)
(52) U.S. Cl.
CPC ............ *G01N 3/34* (2013.01); *G01N 3/12* (2013.01)
(58) Field of Classification Search
CPC ............ G01N 3/12; G01N 2203/0019; G01N 2203/0026; G01N 2203/0256; G01N 2203/0039; G01N 33/24
See application file for complete search history.

(56) References Cited

U.S. PATENT DOCUMENTS

| 11,326,452 B1 * | 5/2022 | Cao ..................... E21D 23/04 |
| 2019/0383714 A1 | 12/2019 | Li et al. |

FOREIGN PATENT DOCUMENTS

| CN | 105675840 A * | 6/2016 | ............ G01N 33/24 |
| CN | 106546484 A * | 3/2017 | ............ G01N 3/08 |

(Continued)

OTHER PUBLICATIONS

Internation Search Report of PCT/CN2022/073324, dated Aug. 31, 2022.

*Primary Examiner* — Natalie Huls

(57) ABSTRACT

A three-dimensional dynamic and static load test system for simulating deep roadway excavation and a method thereof are provided, which relates to the technical field of indoor simulation testing in underground engineering. The system includes a mobile platform, a box body, a support frame, a roadway excavation device, and a data monitoring unit. The system and method of the disclosure can reproduce the whole process of roadway excavation, simulate the multi-directional loading of deep roadway, and restore the real stress state of deep roadway under the influence of dynamic and static load superimposed disturbance. The problem of insufficient research under the condition of unidirectional static loading and lack of multi-directional dynamic and static loading in current large-scale experimental devices has been solved, and the stress and deformation of the surrounding rock of the roadway are reflected in real-time through the data monitoring unit.

9 Claims, 7 Drawing Sheets

(56) References Cited

FOREIGN PATENT DOCUMENTS

| | | | | | |
|---|---|---|---|---|---|
| CN | 106769484 | A | | 5/2017 | |
| CN | 108827578 | A | | 11/2018 | |
| CN | 109100109 | A * | 12/2018 | ............. | G01M 7/08 |
| CN | 109100109 | A | | 12/2018 | |
| CN | 109975129 | A * | 7/2019 | | |
| CN | 210720389 | U * | 6/2020 | | |
| CN | 112461669 | A * | 3/2021 | ............. | G01N 3/02 |
| CN | 112461669 | A | | 3/2021 | |
| CN | 112461670 | A * | 3/2021 | ............. | G01N 3/02 |
| CN | 112461670 | A | | 3/2021 | |
| CN | 112763581 | A * | 5/2021 | ............ | G01N 29/14 |
| IN | 112763581 | A | | 5/2021 | |
| WO | 2019205189 | A1 | | 10/2019 | |

* cited by examiner

US 11,860,135 B2

THREE-DIMENSIONAL DYNAMIC AND STATIC LOAD TEST SYSTEM FOR SIMULATING DEEP ROADWAY EXCAVATION AND METHOD THEREOF

CROSS-REFERENCE TO RELATED APPLICATIONS

This application is a continuation of International Application No. PCT/CN2022/073324 with a filing date of Jan. 22, 2022, designating the United states, and further claims to the benefit of priority from Chinese Application No. 202111483690.7 with a filing date of Dec. 7, 2021. The content of the aforementioned applications, including any intervening amendments thereto, are incorporated herein by reference.

TECHNICAL FIELD

The present disclosure relates to the field of indoor simulation testing technology for underground engineering, specifically to a three-dimensional dynamic and static load test system for simulating deep roadway excavation and a method thereof.

BACKGROUND

In view of the harmfulness and complexity of rock burst, the study of rock burst has become a hot and difficult issue in the field of rock mechanics. Statistical analysis shows that rock burst disasters often occur inside roadway. As the mining depth increases, the mining conditions become more complex, which can easily lead to damage caused by the instability of the surrounding rock of the roadway, and even lead to more significant disasters.

At present, the reason why it is difficult to contain major disasters in deep engineering mining is the lack of a profound study on the mechanism of disaster occurrence, and using the physical similar material simulation test to study underground disaster prevention and control is an effective method. However, the existing physical similar material simulation test systems mostly simulate the stress environment of roadway surrounding rock by unidirectional loading. Under the high crustal stress state, the surrounding rock of deep roadway suffers the multi-directional loading, and unidirectional loading is not enough to fully reflect the real stress state of deep roadway surrounding rock. Next, the existing similar material simulation test systems focus on the stable application of static loads, with little consideration given to the instantaneous dynamic load disturbance behavior of surrounding rock of deep roadway. When the surrounding rock of the roadway is affected by the combined disturbance of dynamic and static loads, the existing test systems cannot accurately simulate the stress conditions of the surrounding rock of the roadway. In addition, the existing physical similarity material simulation test systems are difficult to achieve manual layered excavation and cannot place grouting anchor rods, the experimental device is inconvenient to move and operate, and it is difficult to observe the progressive fracture process of the surrounding rock of the model roadway. It can be seen that the operation and functionality of existing similar material simulation test systems need further improvement.

SUMMARY

The objective of the disclosure is to provide a three-dimensional dynamic and static load test system for simulating deep roadway excavation and a method thereof, reproduce the whole process of roadway excavation, simulate the multi-directional loading of deep roadway and the disturbance caused by the superposition of dynamic and static loads on deep roadway, so as to restore the real stress state of deep roadway.

In order to achieve the above objective, the technical solution adopted by the present disclosure is as follows:

A three-dimensional dynamic and static load test system for simulating deep roadway excavation, including a mobile platform, a box body, a support frame, a roadway excavation device, and a data monitoring unit.

The mobile platform is provided with a support platform which is capable to slide relative to the mobile platform, and the box body is placed on the support platform.

The box body is in a rectangular structure, wherein a similar material model is placed inside the box body, a detachable observation window is arranged on the box body, lateral bearing plates are arranged at the left and right ends of the box body, and an axial bearing plate is arranged at the top inside of the box body.

The support frame is erected at the left, right, and top ends of the mobile platform and the box body.

The left end of the support frame is provided with a plurality of pendulum impact units. Each of the pendulum impact units includes a first impact rod, a swing rod, a pendulum, a first fixed pulley, and a first pull rope, wherein the first impact rod passes through the box body, and is capable to move along horizontal direction, and one end of the first impact rod contacts the lateral bearing plate at the left end of the box body. The upper end of the swing rod is hinged to the support frame, and the lower end of the swing rod is provided with the pendulum. The first fixed pulley is arranged on the support frame. One end of the first pull rope is connected to the pendulum, and the other end of the first pull rope is led out through the first fixed pulley. After pulling the first pull rope and releasing the first pull rope, the swing rod swings relative to the support frame, and the pendulum strikes the other end of the first impact rod.

The left end of the support frame is provided with a plurality of lateral actuators. Each of the lateral actuators is connected to one end of the second impact rod. The second impact rod passes through the box body, the second impact rod is capable to move in a horizontal direction, and the other end of the second impact rod contacts the lateral bearing plate at the left end inside the box body.

The right end of the support frame is provided with a plurality of lateral loading cylinders. The loading end of the lateral loading cylinder passes through the box body, and the loading end of the lateral loading cylinder conducts loading along the horizontal direction. The loading end of the lateral loading cylinder contacts the lateral bearing plate at the right end inside the box body.

The top of the support frame is provided with a plurality of drop hammer impact units. Each of drop hammer impact units includes a third impact rod, a drop hammer, a second fixed pulley, and a second pull rope. The third impact rod passes through the box body, and is capable to move along vertical direction. One end of the third impact rod contacts the axial bearing plate at the top inside of the box body, the second fixed pulley is arranged on the support frame, one end of the second pull rope is connected to the drop hammer, and the other end of the second pull rope is led out through the second fixed pulley. After pulling the second pull rope and releasing the second pull rope, the drop hammer hits the other end of the third impact rod.

The top of the support frame is provided with a plurality of axial actuators. Each of the axial actuators is connected to one end of the fourth impact rod. The fourth impact rod passes through the box body, and the fourth impact rod is capable to move along vertical direction. The other end of the fourth impact rod contacts the axial bearing plate at the top inside of the box body.

The top of the support frame is provided with a plurality of axial loading cylinders, with the loading end of each of the axial loading cylinders passing through the box body. The loading end of each of the axial loading cylinders conducts loading in vertical direction, and the loading end of the axial loading cylinder contacts the axial bearing plate at the top inside of the box body.

The roadway excavation device is used to excavate simulated roadway in similar material model.

The data monitoring unit is used to monitor the parameters of similar material model during the process of excavating the simulated roadway.

The advantageous technical effects of the present disclosure are as follows:

The three-dimensional dynamic and static load test system for simulating deep roadway excavation and a method thereof can reproduce the whole process of roadway excavation, simulate the multi-directional loading of deep roadway, and restore thereat stress state of deep roadway under the influence of dynamic and static load superimposed disturbance. The problem of insufficient research under the condition of unidirectional static loading and lack of multi-directional dynamic and static loading in current large-scale experimental devices has been solved. In addition, the stress and deformation of the surrounding rock of the roadway are reflected in real-time through the data monitoring unit.

DETAILED DESCRIPTION OF THE EMBODIMENTS

Figure 1:
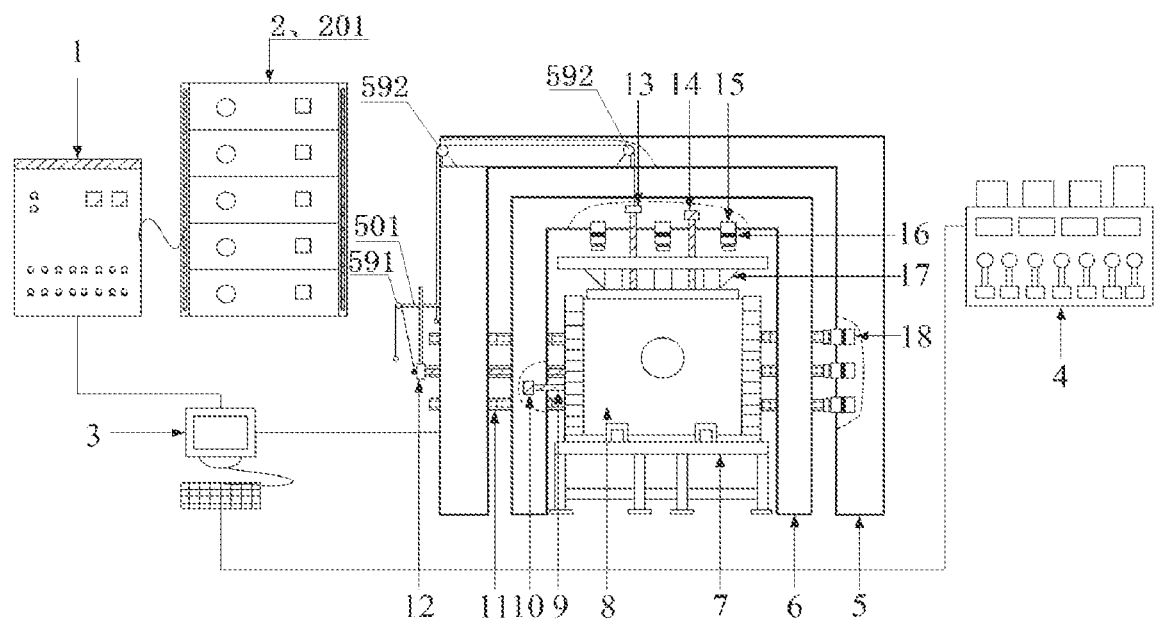
FIG. 1 is the front view of a three-dimensional dynamic and static load test system for simulating deep roadway excavation in an embodiment of the present disclosure.
Figure 2:
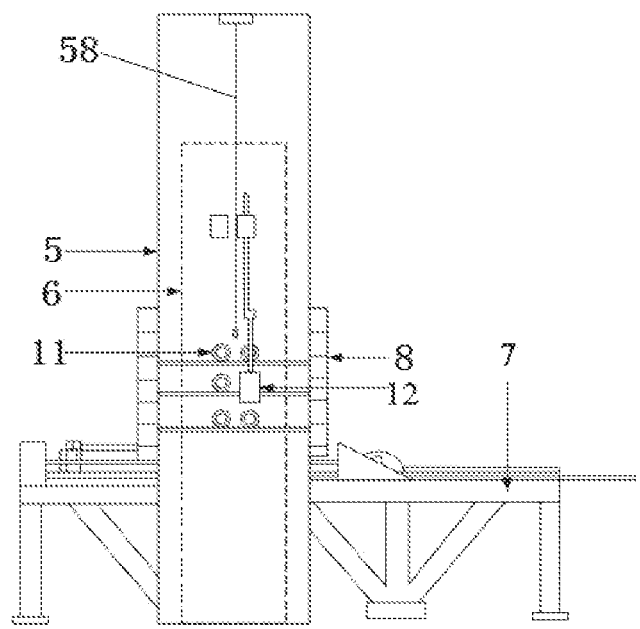
FIG. 2 is a lateral view of a three-dimensional dynamic and static load test system for simulating deep roadway excavation in the embodiment of the present disclosure.
Figure 3:
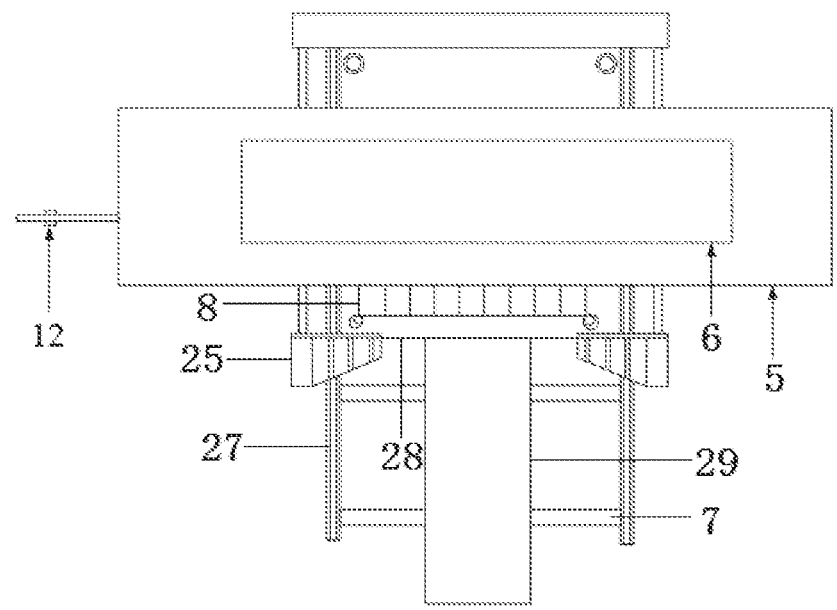
FIG. 3 is a top view of a three-dimensional dynamic and static load test system for simulating deep roadway excavation in the embodiment of the present disclosure.
Figure 4:
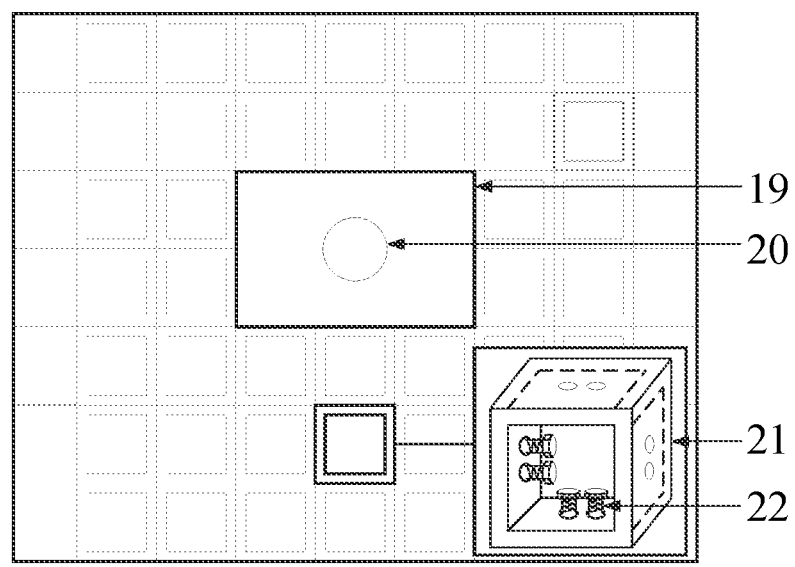
FIG. 4 is the front view of the box body of the embodiment of the present disclosure.
Figure 5:
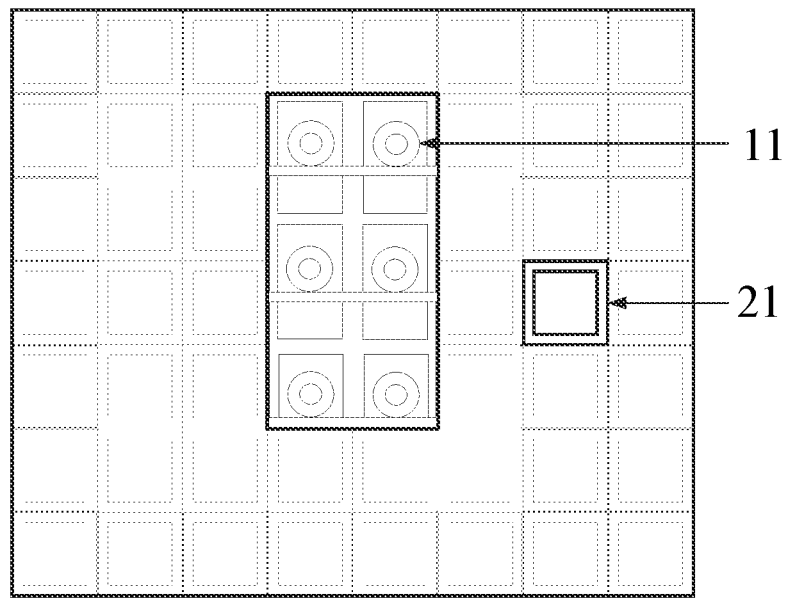
FIG. 5 is a lateral view of the box body of the embodiment of the present disclosure.
Figure 6:
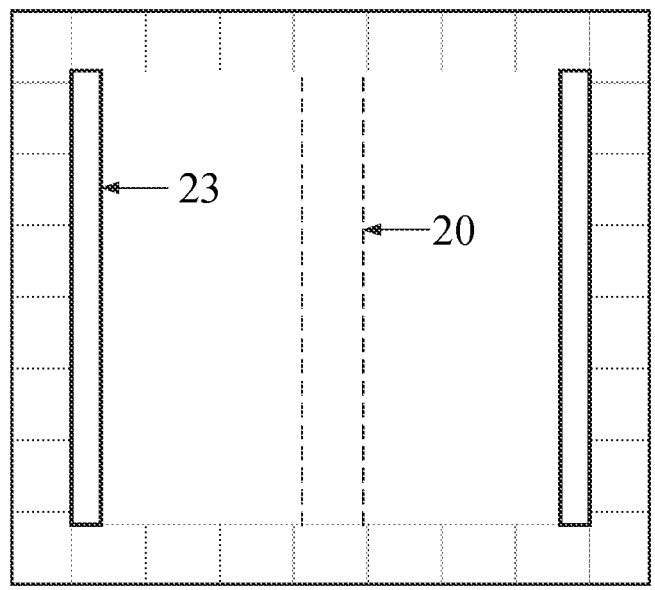
FIG. 6 is a top view of the box body of the embodiment of the present disclosure.
Figure 7:
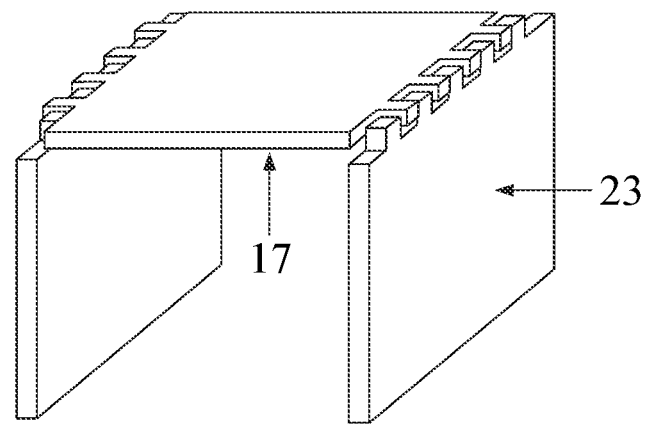
FIG. 7 is a perspective view of a lateral bearing plate and a axial bearing plate in the embodiment of the present disclosure.
Figure 8:
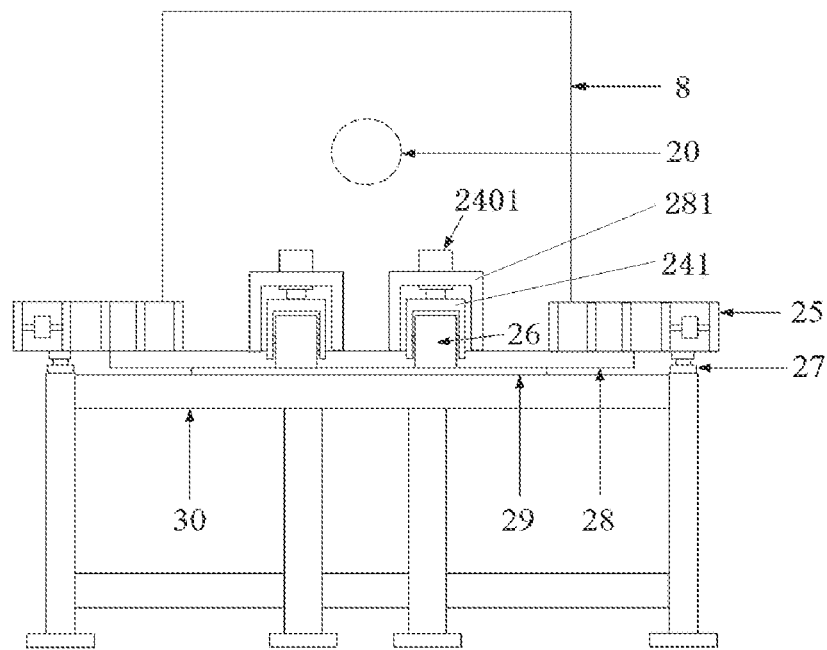
FIG. 8 is a front view of a mobile platform, a support platform, and the box body in the embodiment of the present disclosure.
Figure 9:
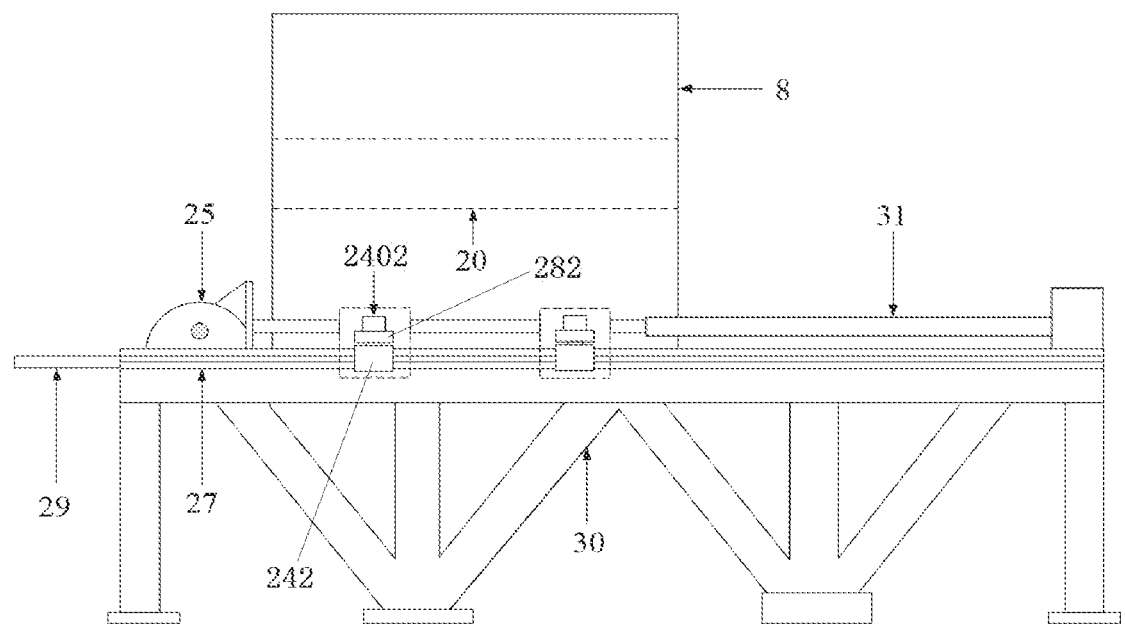
FIG. 9 is a lateral view of the mobile platform, the support platform, and the box body in the embodiment of the present disclosure.
Figure 10:
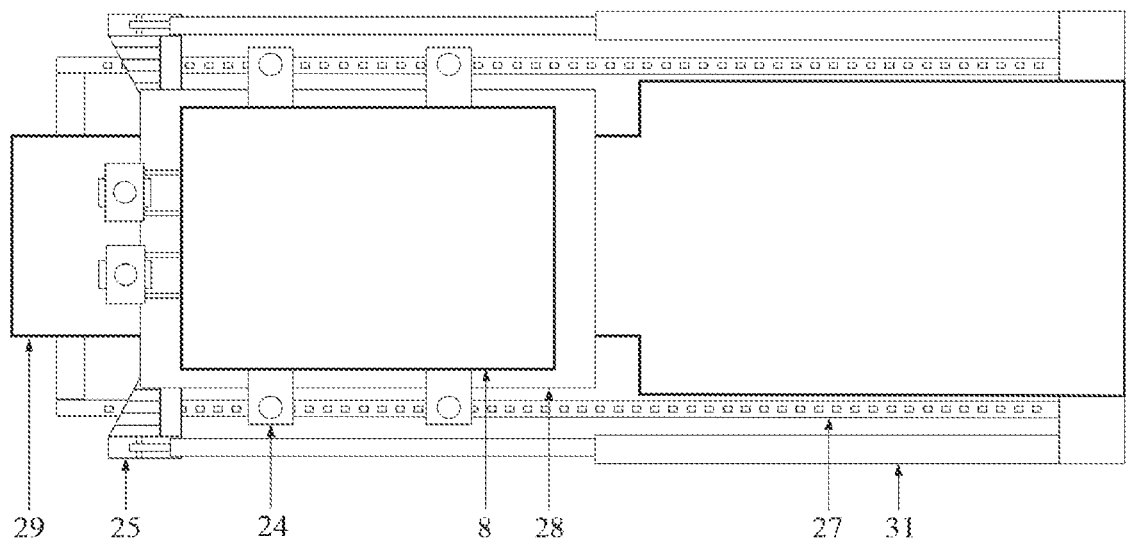
FIG. 10 is a top view of the mobile platform, the support platform, and the box body of the embodiment of the present disclosure.
Figure 11:
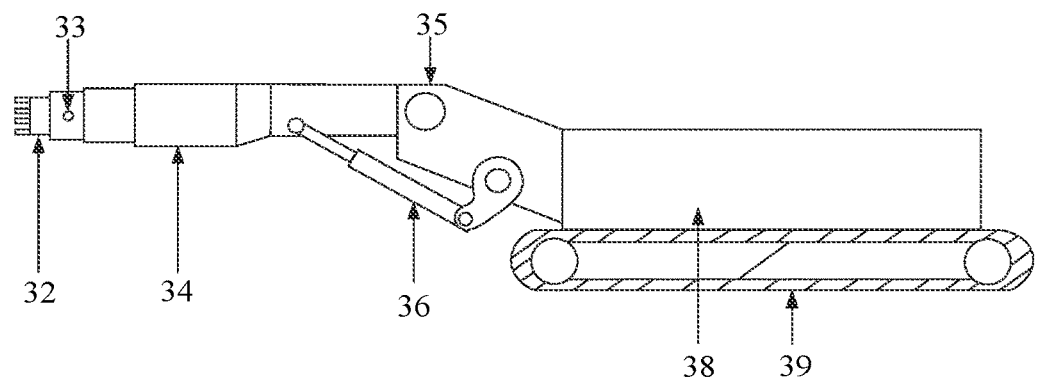
FIG. 11 is a front view of a roadway excavation device in the embodiment of the present disclosure.
Figure 12:
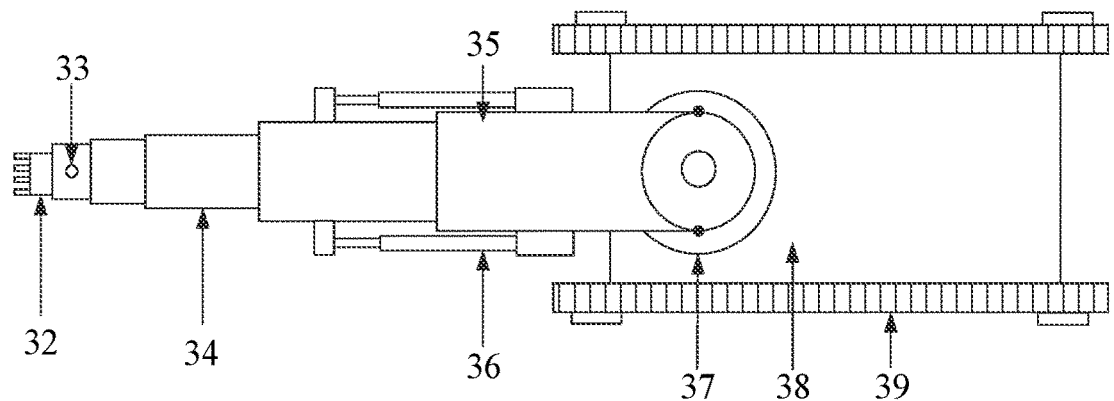
FIG. 12 is a top view of the roadway excavation device in the embodiment of the present disclosure.
Figure 13:
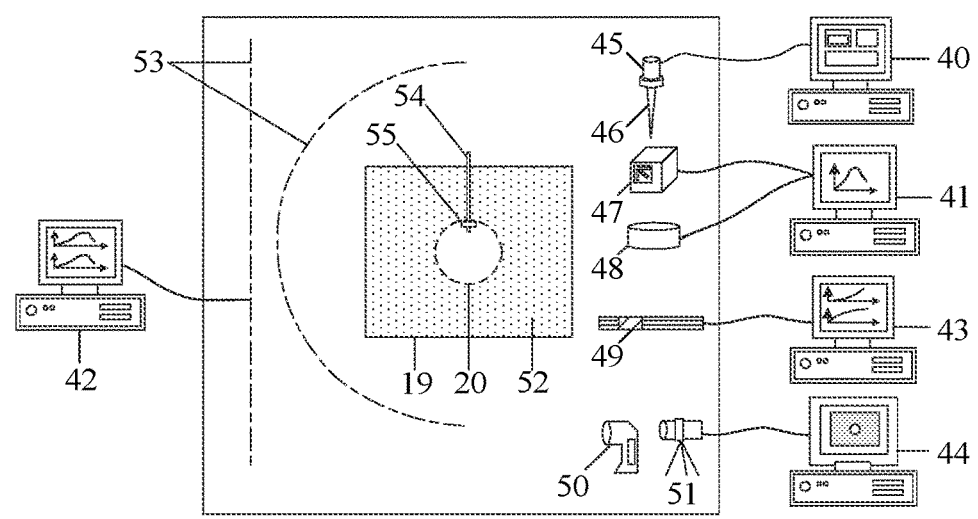
FIG. 13 is the layout diagram of a data monitoring unit in the embodiment of the present disclosure.
Figure 14:
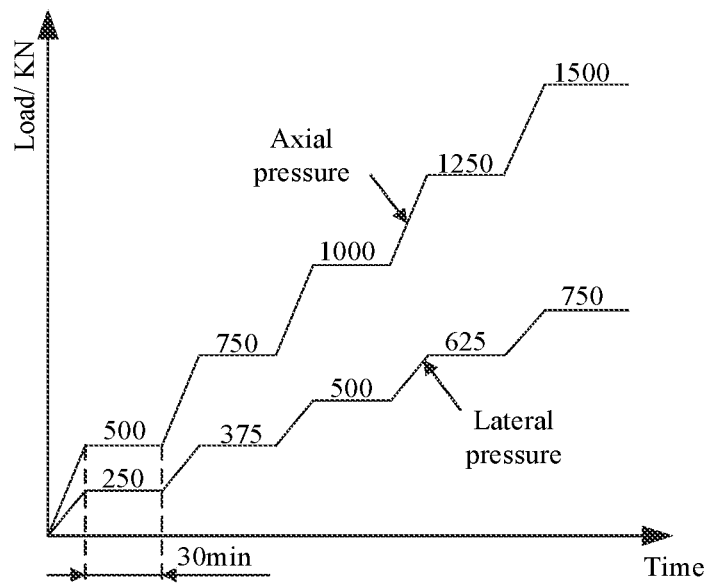
FIG. 14 is a load-time schematic diagram of the model loading scheme using an axial loading cylinder in the embodiment of the present disclosure.
Figure 15:
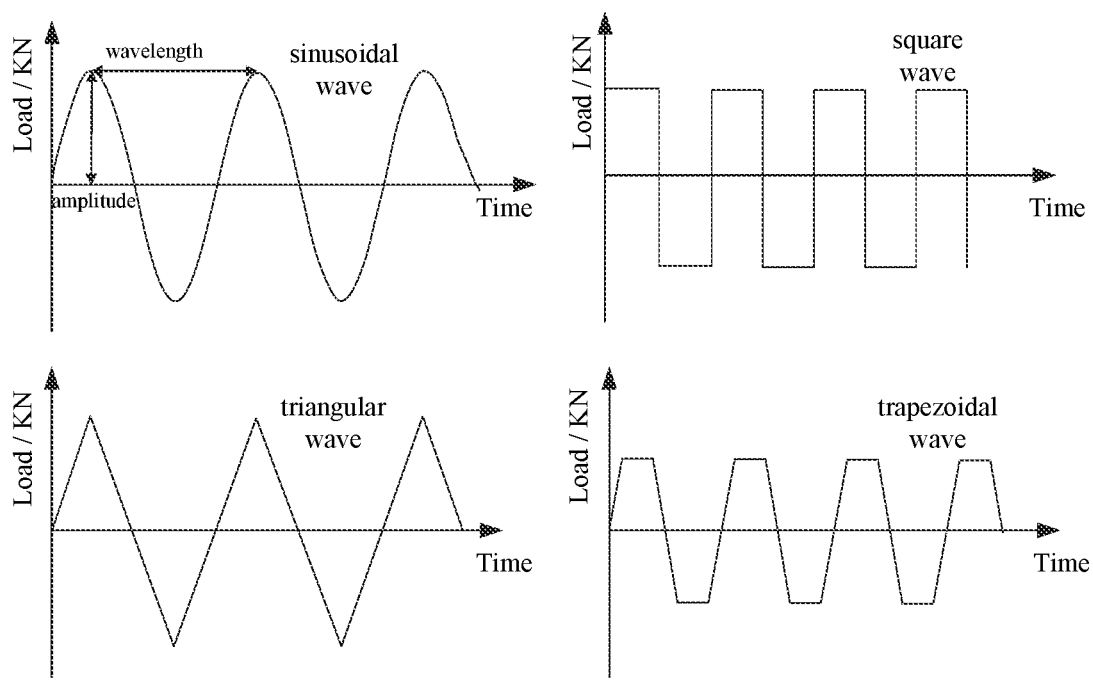
FIG. 15 is a load-time schematic diagram of the scheme shown that the actuator (an axial actuator, a lateral actuator) of the present disclosure applies dynamic loads (axial dynamic load, lateral dynamic load) to the model.

In the embodiment of the present disclosure, a three-dimensional dynamic and static load test system for simulating deep roadway excavation, as shown in FIGS. 1-15.

A three-dimensional dynamic and static load test system for simulating deep roadway excavation is provided, which includes a mobile platform 7, a box body 8, a support frame, a roadway excavation device, a data monitoring unit and etc.

The mobile platform 7 is provided with a support platform 28, the support platform 28 is capable to move relative to the mobile platform 7, and the box body 8 is placed on the support platform 28. The support platform 28 moves relative to the mobile platform 7 to drive the box body 8 to move.

Specifically, the mobile platform 7 includes a support base 30, a long platform 29, and guides rails 27, along platform 29 is arranged in the middle of the support base 30, the long platform 29 extends along a front-rear direction of the support base 30, the guide rails are arranged on the left side and the right side of the support base, and the guide rails extends along the front-rear direction of the support base. The edge positions of the front side and the rear side of the support platform 28 are respectively provided with a first support seat 281. The first support seat 281 is provided with a first lifting oil cylinder 2401, a telescopic end of the first lifting oil cylinder 2401 faces downwards, and the end of the telescopic end of the first lifting oil cylinder 2401 is provided with a wheel seat 241. The wheel seat 241 is rotationally connected with a roller 26, and the roller 26 is located above the long platform 29. After the telescopic end of the first lifting oil cylinder 2401 is extended, the roller 26 contacts the long platform 29. The edge positions of the left side and the right side of the support platform are respectively provided with a second support seat 282. The second support seat 282 is provided with a second lifting oil cylinder 2402, a telescopic end of the second lifting oil cylinder 2402 faces downwards, and the end of the telescopic end of the second lifting oil cylinder 2402 is provided with a slider 242. The slider 242 is slidably connected to the guide rail. The cylinder body of a telescopic oil cylinder 31 is connected to the support base 30, and the telescopic end of the telescopic oil cylinder 31 is connected to the support platform 28 via a connection piece 25.

The box body 8 is a steel structure with a large volume, and the weight of similar material model placed inside the box body 8 is heavy, so it is time-consuming and laborious to move them in manual.

The movement process of the support platform 28 relative to mobile platform 7 is as follows:

1. When it needs the box body 8 to be moved forward with the support platform 28 relative to the mobile platform 7, the telescopic end of the second lifting oil cylinder 2402 on the second support seat 282 is extended to drive the support platform 28 to lift upward; after the support platform 28 is lifted at the set height, the telescopic end of the first lifting oil cylinder 2401 on the first support seat 281 is extended, and the roller 26 contacts the long platform 29; the telescopic end of the second lifting oil cylinder 2402 on the second support seat 282 is retracted to a set distance, so that the slider 242 no longer exerts pressure on the guide rail 27, keeping the slider connected to the guide rail 27 in sliding; the telescopic end of the telescopic oil cylinder 31 is extended to push the roller 26 to roll forward along the long platform 29, to drive the support platform 28 to move forward relative to the mobile platform 7. During the process of moving out, the slider 242 and the guide rail 27 slide together to achieve guidance. After the support platform 28 is moved out, the telescopic ends of the lifting oil cylinders on the first support seat 281 and the second support seat 282 are retracted, so that the support platform 28 is pressed onto the long platform 29, to facilitate the model laying and the placement of sensors by the testing personnel.

2. When it needs the box body 8 to be moved backward with the support platform 28 relative to the mobile platform 7, the telescopic end of the second lifting oil cylinder 2402 on the second support seat 282 is extended to drive the support platform 28 to lift upward; after the support platform 28 is lifted at the set height, the telescopic end of the first lifting oil cylinder 2401 on the first support seat 281 is extended, and the roller 26 contacts the long platform 29; the telescopic end of the second lifting oil cylinder 2402 on the second support seat 282 is retracted to a set distance, so that the slider 242 no longer exerts pressure on the guide rail, keeping the slider 242 connected to the guide rail 27 in sliding; the telescopic end of the telescopic oil cylinder 31 is retracted to push the roller 26 to roll backward along the long platform 29, so as to drive the support platform 28 to move backward relative to the mobile platform 7. During the process of moving in, the slider 242 and the guide rail 27 slide together to achieve guidance. After the support platform 28 is moved in, the telescopic ends of the lifting oil cylinders on the first support seat 281 and second support seat 282 are retracted, so that the support platform 28 is pressed onto the long platform 29 for subsequent testing.

The box body 8 is in a rectangular structure, which is symmetrically distributed in front and back, and left and right. The box body 8 is formed by a plurality of blocks 21, and the plurality of blocks 21 are detachable spliced. The block 21 is made of steel material, with a hollow structure in the middle. Assembly holes are set on the side walls of the block 21, and the adjacent blocks 21 are connected by high-strength bolts 22. In this way, several different specifications and sizes of box body 8 can be formed by splicing the blocks 21 according to the experimental needs. A similar material model is placed inside the box body 8. A observation window 19 is detachably arranged on the box body 8, which is used to observe the deformation and failure mode of surrounding rock through the observation window 19, and the observation window 19 is made of toughened glass material. The lateral bearing plates 23 are arranged at the left end and the right end of the box body 8, and an axial bearing plate 17 is arranged at the top inside of the box body 8. The lateral bearing plate 23 is used to transfer force between the loading end of the lateral loading cylinder 18 and the similar material model, while the axial bearing plate 17 is used to transfer force between the loading end of the axial loading cylinder 15 and the similar material model.

The support frame includes an outer frame 5 and an inner frame 6, both of which are in an n-shaped structure. The support frame is erected at the left, right, and top ends of the mobile platform 7 and the box body 8.

The left end of the support frame is provided with a plurality of pendulum impact units. Each of the plurality of the pendulum impact units includes a first impact rod 91, a swing rod 56, a pendulum 12, a first fixed pulley 591, and a first pull rope 57. The first impact rod 91 passes through the box body 8 and is capable to move along horizontal direction. One end of the first impact rod 91 contacts the lateral bearing plate 23 at the left end inside of the box body 8. The support frame is provided with a support rack 501, the upper end of the swing rod 56 is hinged to the support rack 501, and the lower end of the swing rod 56 is provided with the pendulum 12. The first fixed pulley 591 is arranged on the support rack 501, one end of the first pull rope 57 is connected to the pendulum 12, and the other end of the first pull rope 57 is led out through the first fixed pulley 591. After pulling the first pull rope 57 and releasing the first pull rope 57, the swing rod 57 swings relative to the support rack 501, and the pendulum 12 strikes the other end of the first impact rod 91. One end of the first impact rod 91 impacts the lateral bearing plate 23 at the left end inside the box 8. By changing the swing height of the pendulum 12 through the first pull rope 57, the force of the pendulum 12 hitting the first impact rod 91 is adjusted.

The left end of the support frame is provided with a plurality of lateral actuators 10, each of the lateral actuators 10 is connected to one end of the second impact rod 92, the second impact rod 92 passes through the box body 8, the second impact rod 92 is capable to move in a horizontal direction, and the other end of the second impact rod 92 contacts the lateral bearing plate 23 at the left end inside the box body 8.

The right end of the support frame is provided with a plurality of lateral loading cylinders 18, the loading end of each of the lateral loading cylinders 18 passes through the box body 8, the loading end of each of the lateral loading cylinders 18 conducts loading along the horizontal direction, and the loading end of each of the lateral loading cylinders 18 contacts the lateral bearing plate 23 at the right end inside the box body 8.

The top of the support frame is provided with a plurality of drop hammer impact units, each of drop hammer impact units includes a third impact rod 93, a drop hammer 13, a second fixed pulley 592, and a second pull rope 58. The third impact rod 93 passes through the box body 8 and is capable to move along vertical direction, one end of the third impact rod 93 contacts the axial bearing plate 17 at the top inside of the box body 8, the second fixed pulley 592 is arranged on the outer frame 5 of the support frame, one end of the second pull rope 58 is connected to the drop hammer 13, and the other end of the second pull rope 58 is led out through the second fixed pulley 592. After pulling the second pull rope 58 and releasing the second pull rope 58, the drop hammer 13 hits the other end of the third impact rod 93, so that one end of the third impact rod 93 impacts the axial bearing plate 17 at the top of the inside of the box body 8. By changing the lifting height of the drop hammer 13 through the second pulling rope 58 to adjust the force of the drop hammer 13 hitting the third impact rod 93.

The top of the support frame is provided with a plurality of axial actuators 14, each of the axial actuators 14 is connected to one end of the fourth impact rod 94, the fourth impact rod 94 passes through the box body 8, the fourth impact rod 94 is capable to move along vertical direction, and the other end of the fourth impact rod 94 contacts the axial bearing plate 17 at the top inside the box body 8.

A hollow transmission cylinder 11 is arranged between the support frame and the box body 8, and the first impact rod 91, the second impact rod 92, the third impact rod 93, and the fourth impact rod 94 are all located inside the hollow transmission cylinder 11. In the figures, the hollow transmission cylinder 11 at the positions of the second impact rod 92, the third impact rod 93, and the fourth impact rod 94 is omitted for clearly expression of the second impact rod 92, the third impact rod 93, and the fourth impact rod 94. The guidance of each impact rod is achieved by the hollow transmission cylinder 11. Wherein a threaded hole is provided on the support frame, an external thread is provided on the outer surface of the hollow transmission cylinder 11, and the hollow transmission cylinder 11 is threaded connected to the threaded hole. The hollow transmission cylinder 11 is rotated relative to the threaded hole to adjust the position of the hollow transmission cylinder 11 according to the specifications and dimensions of the box body 8.

The top of the support frame is provided with a plurality of axial loading cylinders 15, wherein the loading end of the axial loading cylinder 15 passes through the box body 8, the loading end of the axial loading cylinders 15 conducts loading in vertical direction, and the loading end of the axial loading cylinder 15 contacts the axial bearing plate 17 at the top inside of the box body 8.

Both the lateral actuator 10 and the axial actuator 14 are set as electro-hydraulic servo actuators, and the lateral actuators 10, the axial actuators 14, the lateral loading cylinders 18, and the axial loading cylinders 15 share a high-pressure pump box 4. The high-pressure pump box 4 provides hydraulic power for the lateral actuators 10, the axial actuators 14, the lateral loading cylinders 18, and the axial loading cylinders 15.

The static load control units 201 are installed in the static load control cabinet 2. The static load control units 201 are respectively connected to the lateral loading cylinder 18 and the axial loading cylinder 15 through signal connections, hydraulic sensors 16 are provided in the lateral loading cylinder 18 and the axial loading cylinder 16, and the static load control units 201 and the hydraulic sensors 16 are connected to the main control unit 3 through signal connections. The main control unit 3 controls the static load control units 201 to perform static loading, unloading, and load holding on the loading ends of the lateral loading cylinder 18 and the axial loading cylinder 15, and can also achieve servo control, displacement control, stress control, and other loading methods. The hydraulic sensors 16 provide real-time feedback on the oil pressure inside the lateral loading cylinder 18 and the axial loading cylinder 15. The hydraulic sensors 16 will realize safety warning during the loading process if the oil pressure inside the oil cylinder is over the preset value.

The dynamic load control unit is connected to the lateral actuator 10 and the axial actuator 14 through signals, and the dynamic load control unit is connected to the main control unit 3 through signals. The main control unit 3 controls the dynamic load control unit to apply a set impact form of dynamic loads to the lateral actuator 10 and the axial actuator 14, so as to change the force and frequency of impact.

The lateral loading cylinder 18 and the axial loading cylinder 15 apply static load to the similar material model to simulate initial crustal stress. The lateral actuator 10 and the axial actuator 14 apply vibration to the similar material model to simulate continuous disturbances in surrounding roadway excavation and mining engineering of surrounding working faces. The pendulum impact unit and the drop hammer impact unit impact the similar material model to simulate the instantaneous disturbances of geological structure sudden change caused by fault slip and roof failure.

A power supply 1 is used to supply power to the main control unit 3, the static load control units 201, the dynamic load control unit, and the data monitoring unit.

The roadway excavation device is configured to excavate simulated roadway 20 in the similar material model. Specifically, the roadway excavation device includes a mobile chassis 39, a driving mechanism, a rotary table 37, a rotation driving mechanism, a cantilever rack 35, a multi-stage oil cylinder 34, a support oil cylinder 36, a rotary drill bit 32, a rotary driving mechanism, a stress sensor 33, and an excavation control unit. The mobile chassis 39 is driven to move by a driving mechanism, the rotary table 37 is rotatably connected to the mobile chassis 39, the rotary table 37 is driven to rotate by the driving mechanism, the cantilever rack 35 is installed on the rotary table 37, the cantilever rack 35 is arranged on the rotary table 37, and a cylinder end of the multi-stage oil cylinder 34 is hinged with the cantilever rack 35. One end of the support oil cylinder 36 is hinged with the cantilever rack 35, and the other end of the support oil cylinder 36 is hinged with the cylinder end of the multi-stage oil cylinder 34. The end of the telescopic end of the multi-stage oil cylinder 34 is provided with the rotary drill bit 32, the rotary drill bit 32 is driven to rotate by a rotary driving mechanism, and a stress sensor 33 is arranged on the rotary drill bit 32. The excavation control unit 38 is respectively connected to the driving mechanism, the rotation driving mechanism, the multi-stage oil cylinder 34, the support oil cylinder 36, the rotary driving mechanism, and the stress sensor 33 through signals, and the excavation control unit 38 is connected to the main control unit 3 through signals.

The main control unit 3 controls the driving mechanism through the excavation control unit 38 to drive the mobile chassis 39 forward, backward, stop, or turn; controls the rotation driving mechanism to drive the rotary table 37 to rotate at a set angle relative to the mobile chassis 39 to adjust the excavation angle; controls the expansion and contraction of the multi-stage oil cylinder 34 to drive the rotary drill bit 32 forward or backward; controls the expansion and contraction of the support oil cylinder 36 to drive the swing of the multi-stage oil cylinder 34 to adjust the pitch angle of the multi-stage oil cylinder 34; controls the rotation driving mechanism to drive the rotation of the rotary drill bit 32 to excavate the simulated roadway 20, and monitor the drilling pressure during the excavation of the simulated roadway 20 in real-time through the stress sensor 33.

The data monitoring unit is configured to monitor the parameters of the similar material model during the process of excavating the simulated roadway 20.

Specifically, the data monitoring unit includes an acoustic emission monitoring unit, a stress monitoring unit, a strain monitoring unit, a displacement monitoring unit and a deformation monitoring unit.

The acoustic emission monitoring unit includes an acoustic emission monitoring control host 40 and an acoustic emission probe 45, The acoustic emission probe 45 is set on the steel nail 46, and the steel nail 46 is inserted into the similar material model to arrange the acoustic emission probe 45 at different positions inside the similar material model (including any position inside the simulated roadway 20). The acoustic emission probe 45 is connected to the acoustic emission monitoring control host 40 through a signal cable. Using the acoustic emission monitoring unit to monitor and simulate the development of cracks in the surrounding rock of roadway 20 before, during, and after excavation.

The stress monitoring unit includes a stress monitoring control host 41, a strain gauge 47, and a soil pressure box 48. The strain gauge 47 and the soil pressure box 48 are arranged at different positions in the similar material model, and the strain gauge 47 and the soil pressure box 48 are connected to the stress monitoring control host 41 through a signal cable. The stress monitoring unit is used to monitor the stress changes in local areas of the similar material model, wherein the strain gauge 47 is used to monitor the stress situation in the local X, Y, and Z directions of the model, and the soil pressure box 48 is used to monitor the stress situation in a single direction of the model.

The strain monitoring unit includes a strain monitoring control host 42 and an optical fiber sensor 53, the optical fiber sensor 53 is arranged at different positions in the similar material model, the optical fiber sensor 53 is connected to the strain monitoring control host 42 through a signal cable. The strain monitoring unit is used to monitor the strain changes in the model area and local range. The optical fiber sensor 53 is buried around the model or roadway to monitor the strain (one-dimensional strain) of a certain measuring line, and can be arranged vertically or bent according to the monitoring requirements.

The displacement monitoring unit includes a displacement monitoring control host 43 and a grating displacement sensor 49, the grating displacement sensor 49 is arranged at different positions in the similar material model, and the grating displacement sensor 49 is connected to the displacement monitoring control host 43 through a signal cable. The displacement monitoring unit is used to monitor the displacement changes in local areas of the model. The grating displacement sensor 49 can be placed around the roadway to measure the displacement of the surrounding rock of the roadway, or the grating displacement sensor 49 can be placed at the edge of the model to measure the overall deformation of the model.

The deformation monitoring unit includes a deformation monitoring control host 44, a speckle camera 51 and a 3D scanner 50, and the speckle camera 51 and the 3D scanner 50 are connected to the deformation monitoring control host 44 through a signal cable. The deformation monitoring unit is used to monitor the deformation of the model area or the internal deformation of the roadway. The scattered spots 52 is uniformly sprayed on the model surface, and the speckle camera 51 is used to monitor the evolution process of the model surface deformation (two-dimensional strain) field through the observation window 19. The 3D scanner 50 is used to scan the inner wall of the roadway and analyze the deformation (3D strain) of the roadway.

In the embodiment of the present disclosure, a three-dimensional dynamic and static load test method for simulating deep roadway excavation is further provided, which applies the three-dimensional dynamic and static load test system for simulating deep roadway excavation mentioned above, the method including:

Step 1: Experimental Scheme Design

Firstly, developing a experimental scheme for this experiment, including the volume of box body 8, the type of excavation roadway, the material of the model, the loading plan, and the monitoring plan. After determining the experimental plan, assemble box body 8 using blocks 21. After the assembly of box body 8 is completed, placing the lateral bearing plates 23 on the left and right sides inside the box body 8, and installing the observation windows 19 in front and behind the box body 8.

Step 2: Model Laying and Sensor Layout

Moving the box body 8 forward with the support platform 28 relative to the mobile platform 7, adjusting a material ratio based on mechanical parameters and a similarity ratio of different rock layers, and laying materials to form a similar material model inside the box body 8; specifically, manual laying is used to adjust the material ratio based on the mechanical parameters and similarity ratio of different rock layers; layered laying is used, and each layer of material is compacted to ensure that the similar material model has sufficient stiffness to maintain uniform force transmission; burying the acoustic emission probe 45, the strain gauge 47, the soil pressure box 48, the optical fiber sensor 53, and the grating displacement sensor 49 in corresponding positions within the similar material model during the material laying process; after the material laying is completed, an axial bearing plate 17 is placed above the similar material model to shape the model, and the similar material model is placed for a set time (2-3 weeks); after the similar material model is air dried and formed, removing the observation windows 19, spraying scattered spots 52 on a simulated roadway excavation position of the similar material model, then reinstalling the observation windows 19 on the box body 8, and then moving the box body 8 backward with the support platform 28 relative to the mobile platform 7.

Step 3. Initial Crustal Stress Simulation

According to the experimental scheme, loading the similar material model to simulate an initial crustal stress state of roadway excavation, wherein the loading method is hierarchical loading under stress control, using the lateral loading cylinders 18 and the axial loading cylinders 15 to hierarchical synchronized load to the similar material model, and maintaining loading for a set time (about 30 min) after completing each level of loading.

Step 4: Roadway Excavation Simulation

Using the roadway excavation device to excavate a simulated roadway 20 in the similar material model. After excavating one footage of the simulated roadway 20 by the excavation device, different lengths of steel sticks 54 are used to simulate anchor rod (anchor cable) support. A force gauge 55 is installed at the bottom of the steel stick 54 to monitor the force status of the anchor rod (anchor cable) in real-time through the force gauge 55.

Step 5: Dynamic Load Simulation

Setting up the impact form (including parameters such as waveform, wavelength, frequency, amplitude, etc.) of the axial actuator 14 after the excavation of the simulated roadway 20 is completed, and then applying the axial dynamic load to the similar material model through the axial actuator 14; setting up the impact form (including parameters such as waveform, wavelength, frequency, amplitude, etc.) of the lateral actuator 10 and then applying lateral dynamic load to the similar material model through the lateral actuator 10; applying axial impact to the similar material model through the drop hammer impact unit; applying lateral impact to the similar material model through the pendulum impact unit. There are several axial actuators 14, lateral actuators 10, drop hammer impact units, and pendulum impact units, all of which transmit dynamic loads to the internal model through each impact rod, and the impact position can be changed.

During steps 3 to 5, the data monitoring unit is used to monitor the parameters of the similar material model. Specifically, the acoustic emission monitoring unit is used to monitor the development of surrounding rock fissures before, during and after the excavation of the simulated roadway 20, the stress monitoring unit is used to monitor the stress change in the local area of the model, the strain monitoring unit is used to monitor the strain change in the model area and local area, the displacement monitoring unit is used to monitor the displacement change in the local area of the model, and the deformation monitoring unit is used to monitor the deformation in the model area or the internal deformation of the roadway.

In addition, the long-term load holding function of static loading (the lateral loading cylinder 18 and the axial loading cylinder 15) is used to apply crustal stress to the model, and the monitoring system is used to observe the stress, displacement and deformation of the surrounding rock of the roadway for a long time to achieve creep testing.

At this point, a detailed description of this embodiment has been provided in conjunction with the accompanying drawings. Based on the above description, those skilled in the art should have a clear understanding of the three-dimensional dynamic and static load test system used to simulate deep roadway excavation of the present disclosure.

The three-dimensional dynamic and static load test system and method for simulating deep roadway excavation can reproduce the whole process of roadway excavation, simulate the multi-directional loading of deep roadway, and restore the real stress state of deep roadway under the influence of dynamic and static load superimposed disturbance. The problem of insufficient research under the condition of unidirectional static loading and lack of multi-directional dynamic and static loading in current large-scale experimental devices has been solved. In addition, the stress and deformation of the surrounding rock of the roadway are reflected in real-time through the data monitoring unit.

What is claimed is:

1. A three-dimensional dynamic and static load test system for simulating deep roadway excavation, comprising a mobile platform, a box body, a support frame, a roadway excavation device, a data monitoring unit, a dynamic load control unit, and a main control unit, wherein the mobile platform is provided with a support platform, the support platform is capable to move relative to the mobile platform, and the box body is placed on the support platform;

the box body is in a rectangular structure, a similar material roadway model is placed inside the box body, a detachable observation window is arranged on the box body, lateral bearing plates are respectively arranged at a left end and a right end inside of the box body, and an axial bearing plate arranged at a top inside of the box body;

the support frame is erected at the mobile platform and a left end, a right end, and a top end of the box body;

a left end of the support frame is provided with a plurality of pendulum impact units, each of the plurality of pendulum impact units comprises a first impact rod, a swing rod, a pendulum, a first fixed pulley, and a first pull rope, wherein the first impact rod passes through the box body and is capable to move along horizontal direction; one end of the first impact rod contacts the lateral bearing plate at the left end inside of the box body; an upper end of the swing rod is hinged to the support frame, and a lower end of the swing rod is provided with the pendulum; the first fixed pulley is arranged on the support frame, one end of the first pull rope is connected to the pendulum, and an other end of the first pull rope is led out through the first fixed pulley; after pulling the first pull rope and releasing the first pull rope, the swing rod swings relative to the support frame, and the pendulum strikes an other end of the first impact rod;

the left end of the support frame is provided with a plurality of lateral actuators, each of the plurality of lateral actuators is connected to one end of a second impact rod, the second impact rod passes through the box body, the second impact rod is capable to move in horizontal direction, and an other end of the second impact rod contacts the lateral bearing plate at the left end inside the box body;

a right end of the support frame is provided with a plurality of lateral loading cylinders, a loading end of each of the plurality of lateral loading cylinders passes through the box body, the loading end of each of the lateral loading cylinders conducts loading along horizontal direction, the loading end of each of the lateral loading cylinders contacts the lateral bearing plate at the right end inside the box body;

a top of the support frame is provided with a plurality of drop hammer impact units, each of the plurality of drop hammer impact units comprises a third impact rod, a drop hammer, a second fixed pulley, and a second pull rope, wherein the third impact rod passes through the box body and is capable to move along vertical direction, one end of the third impact rod contacts the axial bearing plate at the top inside of the box body, the second fixed pulley is arranged on the support frame, one end of the second pull rope is connected to the drop hammer, and the other end of the second pull rope is led out through the second fixed pulley; after pulling the second pull rope and releasing the second pull rope, the drop hammer hits an other end of the third impact rod;

the top of the support frame is provided with a plurality of axial actuators, each of the plurality of axial actuators is connected to one end of a fourth impact rod, the fourth impact rod passes through the box body, the fourth impact rod is capable to move along the vertical direction, and an other end of the fourth impact rod contacts the axial bearing plate at the top inside of the box body;

both the lateral actuators and the axial actuators are set as electro-hydraulic servo actuators, and the lateral actuators, the axial actuators, the lateral loading cylinders, and the axial loading cylinders share a high-pressure pump box;

the dynamic load control unit is connected to the lateral actuators and the axial actuators through signals, and the dynamic load control unit is connected to the main control unit through signals;

the main control unit controls the dynamic load control unit to apply a set impact form of dynamic loads to the lateral actuators and the axial actuators and change the impact force and frequency; the lateral actuators and the axial actuators apply axial dynamic loads to the similar material roadway model to simulate continuous disturbances in surrounding roadway excavation and mining engineering of surrounding working faces;

the top of the support frame is provided with a plurality of axial loading cylinders, a loading end of each of the plurality of axial loading cylinders passes through the box body, the loading end of each of the axial loading cylinders conducts loading along vertical direction, and the loading end of each of the axial loading cylinders contacts the axial bearing plate at the top inside of the box body;

the roadway excavation device is configured to excavate simulated roadway in the similar material roadway model; and the data monitoring unit is configured to monitor parameters of the similar material roadway model during a process of excavating the simulated roadway.

2. The three-dimensional dynamic and static load test system for simulating deep roadway excavation according to claim 1, wherein the data monitoring unit comprises an acoustic emission monitoring unit, a stress monitoring unit, a strain monitoring unit, a displacement monitoring unit and a deformation monitoring unit, wherein the acoustic emission monitoring unit comprises an acoustic emission monitoring control host and an acoustic emission probe, the acoustic emission probe is arranged at different positions in the similar material roadway model, and the acoustic emission probe is connected to the acoustic emission monitoring control host through a signal cable;

the stress monitoring unit comprises a stress monitoring control host, a strain gauge, and a soil pressure box, the strain gauge and the soil pressure box are arranged at different positions in the similar material roadway model, and the strain gauge and the soil pressure box are connected to the stress monitoring control host through a signal cable;

the strain monitoring unit comprises a strain monitoring control host and an optical fiber sensor, the optical fiber sensor is arranged at different positions in the similar material roadway model, and the optical fiber sensor is connected to the strain monitoring control host through a signal cable;

the displacement monitoring unit comprises a displacement monitoring control host and a grating displacement sensor, the grating displacement sensor is arranged at different positions in the similar material roadway model, and the grating displacement sensor is connected to the displacement monitoring control host through a signal cable; and the deformation monitoring unit comprises a deformation monitoring control host, a speckle camera and a 3D scanner, and the speckle camera and the 3D scanner are connected to the deformation monitoring control host through a signal cable.

3. The three-dimensional dynamic and static load test system for simulating deep roadway excavation according to claim 1, wherein the mobile platform comprises a support base, a long platform, and guide rails, a long platform is arranged in a middle of the support base, the long platform extends along a front-rear direction of the support base, the guide rails are arranged on a left side and a right side of the support base, and the guide rails extend along the front-rear direction of the support base;

edge positions of a front side and a rear side of the support platform are respectively provided with a first support seat, the first support seat is provided with a first lifting oil cylinder, a telescopic end of the first lifting oil cylinder faces downwards, an end of the telescopic end of the first lifting oil cylinder is provided with a wheel seat, the wheel seat is rotationally connected with a roller, the roller is located above the long platform; after the telescopic end of the first lifting oil cylinder is extended, the roller contacts the long platform;

edge positions of a left side and a right side of the support platform are respectively provided with a second support seat, the second support seat is provided with a second lifting oil cylinder, a telescopic end of the second lifting oil cylinder faces downwards, an end of the telescopic end of the second lifting oil cylinder is provided with a slider, and the slider is slidably connected to each of the guide rails;

a telescopic oil cylinder is connected between the support base and the support platform.

4. The three-dimensional dynamic and static load test system for simulating deep roadway excavation according to claim 1, wherein a hollow transmission cylinder is arranged between the support frame and the box body, and each first impact rod, each second impact rod, each third impact rod, and each fourth impact rod are all located inside the hollow transmission cylinder.

5. The three-dimensional dynamic and static load test system for simulating deep roadway excavation according to claim 4, wherein a threaded hole is provided on the support frame, an external thread is provided on an outer surface of the hollow transmission cylinder, and the hollow transmission cylinder is threaded connected to the threaded hole.

6. The three-dimensional dynamic and static load test system for simulating deep roadway excavation according to claim 1, wherein the box body is formed by a plurality of blocks, and the plurality of blocks are detachable spliced.

7. The three-dimensional dynamic and static load test system for simulating deep roadway excavation according to claim 1, wherein the three-dimensional dynamic and static load test system further comprises static load control units, wherein the static load control units are respectively connected to the lateral loading cylinders and the axial loading cylinders through signal connections, hydraulic sensors are provided in the lateral loading cylinders and the axial loading cylinders, and the static load control units and the hydraulic sensors are connected to the main control unit through signal connections.

8. The three-dimensional dynamic and static load test system for simulating deep roadway excavation according to claim 7, wherein the roadway excavation device comprises a mobile chassis, a driving mechanism, a rotary table, a rotation driving mechanism, a cantilever rack, a multi-stage oil cylinder, a support oil cylinder, a rotary drill bit, a rotary driving mechanism, a stress sensor, and an excavation control unit, wherein the mobile chassis is driven to move by the driving mechanism, the rotary table is rotatably connected to the mobile chassis, the rotary table is driven to rotate by the driving mechanism, the cantilever rack is arranged on the rotary table, the cantilever rack is arranged on the rotary table, a cylinder end of the multi-stage oil cylinder is hinged with a cantilever rack, one end of the support oil cylinder is hinged with the cantilever rack, an other end of the support oil cylinder is hinged with the cylinder end of the multi-stage oil cylinder, an end of a telescopic end of the multi-stage oil cylinder is provided with the rotary drill bit, the rotary drill bit is driven to rotate by the rotary driving mechanism, a stress sensor is arranged on the rotary drill bit, the excavation control unit is respectively connected to the driving mechanism, the rotation driving mechanism, the multi-stage oil cylinder, the support oil cylinder, the rotary driving mechanism, the stress sensor through signals, and the excavation control unit is connected to the main control unit through signals.

9. A three-dimensional dynamic and static load test method for simulating deep roadway excavation, which applies the three-dimensional dynamic and static load test system for simulating deep roadway excavation according to claim 2, the method comprising:

step 1: model laying and sensor layout moving the box body forward with the support platform relative to the mobile platform, adjusting a material ratio based on mechanical parameters and a similarity ratio of different rock layers, and laying materials to form the similar material roadway model inside the box body; burying the acoustic emission probe, the strain gauge, the soil pressure box, the optical fiber sensor, and the grating displacement sensor in corresponding positions within the similar material roadway model during a process of material laying; placing the similar material roadway model for a set time after the material laying is completed; after the similar material roadway model is air dried and formed, removing the observation window, spraying scattered spots on a simulated roadway excavation position of the similar material roadway model, then reinstalling the observation window on the box body, and then moving the box body backward with the support platform relative to the mobile platform;

step 2: initial crustal stress simulation according to the experimental scheme, loading the similar material roadway model to simulate an initial crustal stress state of roadway excavation, wherein the loading method is hierarchical loading under stress control, using the lateral loading cylinders and the axial loading cylinders to hierarchical synchronized load on the similar material roadway model, and maintaining loading for a set time after completing each level of loading;

step 3: roadway excavation simulation using the roadway excavation device to excavate a simulated roadway in the similar material roadway model, the excavation parameters of the simulated roadway are set according to the similarity ratio, the simulated roadway excavated by the roadway excavation device is supported by steel rods or anchor cables;

step 4: dynamic load simulation setting up a impact form of the axial actuators after the simulated roadway excavation is completed, and then applying the axial dynamic loads to the similar material roadway model through the axial actuators; setting up a impact form of the lateral actuators and then applying lateral dynamic loads to the similar material roadway model through the lateral actuators; applying axial impacts to the similar material roadway model through the drop hammer impact units; applying lateral impacts to the similar material roadway model through the plurality of pendulum impact units;

during step 2 to step 4, using the data monitoring unit to monitor the parameters of the similar material roadway model.

* * * * *